United States Patent [19]
Battenfield

[11] Patent Number: 5,364,361
[45] Date of Patent: Nov. 15, 1994

[54] KNEE BURSA DRAINING TEMPLATE AND CANNULATED NEEDLE FOR USE THEREWITH

[76] Inventor: Harold L. Battenfield, 4414 S. Zunis, Tulsa, Okla. 74105

[21] Appl. No.: 145,062

[22] Filed: Oct. 26, 1993

[51] Int. Cl.$^5$ .............................................. A61M 5/00
[52] U.S. Cl. .................................................. 604/116
[58] Field of Search .................. 604/116; 40/299, 908; 132/319; D10/64

[56] References Cited

U.S. PATENT DOCUMENTS

| | | | |
|---|---|---|---|
| 2,097,039 | 10/1937 | Peterson | 128/347 |
| 2,245,350 | 6/1941 | Marshall | 33/189 |
| 3,542,022 | 11/1970 | Bartnik | 128/2.215 |
| 3,547,121 | 12/1970 | Cherry | 128/215 |
| 3,999,504 | 12/1976 | Kearse | 116/121 |
| 4,228,796 | 10/1980 | Gardiner | 128/215 |
| 4,362,157 | 12/1982 | Keeth | 128/215 |
| 4,733,661 | 3/1988 | Palestrant | 604/116 |
| 4,781,678 | 11/1988 | Couët | 128/215 |
| 4,883,053 | 11/1989 | Simon | 604/116 |
| 5,102,391 | 4/1992 | Palestrant | 604/116 |
| 5,123,907 | 6/1992 | Romaine | 604/116 |

FOREIGN PATENT DOCUMENTS 2202445  9/1988  United Kingdom ............... 604/116

*Primary Examiner*—John G. Weiss
*Attorney, Agent, or Firm*—Catalano, Zingerman & McKay

[57] ABSTRACT

The template of this invention includes a flexible sheet with indicia thereon to identify the proper sites and instruction of the proper method of insertion of a cannulated needle to drain a distended human knee bursa, A cannulated needle is used for draining the bursa which includes a rigid needle and a flexible cannula through which the rigid needle is inserted to be attached to a hypodermic syringe. The cannula has a plurality of apertures on its leading end which facilitate drainage by reducing the chance of clogging or blocking of the opening of the cannula.

13 Claims, 2 Drawing Sheets

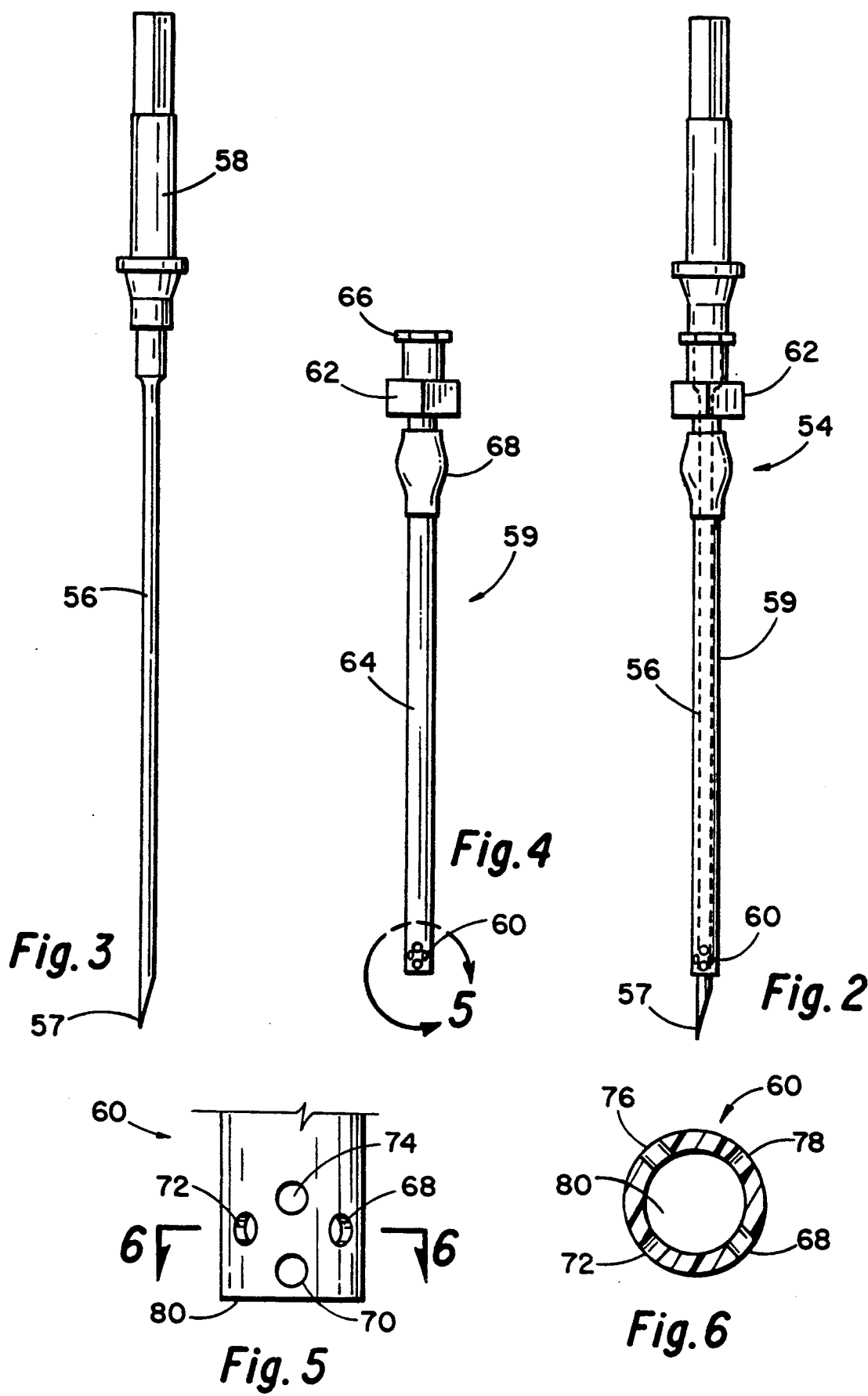

KNEE BURSA DRAINING TEMPLATE AND CANNULATED NEEDLE FOR USE THEREWITH

BACKGROUND OF THE INVENTION

1. Field of the Invention

This invention relates to a template and cannulated needle for use in the medical arts to identify proper hypodermic insertion sites and technique, specifically to drain fluid from a distended painful bursa in the knee.

2. Description of the Related Art

Bursa, usually found near joints, reduce friction between either skin and underlying bones or tendons and bones that must contact each other through body movement. Bursa contain lubricating fluid to reduce such friction. A large number of people, who may either injure their knee joint or irritate the bursa from pressure on the knee joint, are afflicted with a condition where a bursa of a knee becomes filled with blood or synovial fluid, and thus painfully distended. Such a condition causes discomfort, sometimes severe, as well as a limitation of the range of movement of the knee which often requires the bursa to be drained of the fluid.

A physician faced with a patient having a distended bursa must know the proper sites on the leg for hypodermic insertion of the draining apparatus, such as a needle. A need has therefore developed in the medical community for a device which indicates these proper sites.

General Practice or Emergency Room physicians generally have little, or no, training in the proper method of draining a distended bursa. When a knee bursa is not filled with fluid, it is very difficult, if not impossible, to locate. In training, medical students frequently learn anatomy from cadavers where the body fluids have been drained such that the knee bursa have little or no fluid contained within them. Consequently, trained physicians frequently have little knowledge of the proper sites, the best technique, or angles for insertion of a drainage apparatus.

A needle is the common apparatus presently used for draining knee bursa. Insertion of a needle in draining the bursa, however, is a very painful procedure for the patient. As the bursa contracts from fluid being drained, the needle will often contact the bursa inner wall, causing additional discomfort. Additionally, such contact, or other material commonly within the fluid, will clog the single opening of the needle. When the needle becomes clogged, it must then be removed and either cleaned or replaced before the drainage procedure can be resumed. Such removal and reinsertion adds to the duration of the discomfort to the patient plus increase the possibility of infection.

A need, therefore, also exists in the medical art for a bursa drainage device which is resistant to clogging and which is flexible so as to cause less discomfort to the patient.

SUMMARY OF THE INVENTION

The template of this invention is constructed of flexible material so that it may be folded for packaging and transport and then unfolded for use. Indicia are contained on the template for locating it on a human leg over the knee area. This locating indicia includes patella indicium and tibia indicium which are placed over the patella and tibia, respectively, of the patient's leg.

Insertion indicia on the template identify the proper sites and angles of insertion of a device used to drain the knee bursa of fluid. The insertion indicia are placed on the template such that when the patella and tibia indicia are overlaid upon the patella and tibia of the leg, the insertion indicia will overlay the proper insertion sites. The insertion indicia also include instruction of the proper angle of hypodermic insertion of a drainage device into the distended bursa.

A plan view diagram may be placed on the template illustrating the template properly draped over the knee area of a human leg. The patella and tibia indicia are shown properly overlaid upon their respective anatomical features of the leg. The plan view diagram then also illustrates the insertion indicia as they overlay the proper sites of hypodermic insertion of the device used to drain the distended bursa.

A lateral view diagram may also be placed on the template which illustrates the proper point and angle of insertion of a drainage device into the fluid filled bursa. A cut-away of a human leg is depicted with its tibia, femur, tendons, patella, and distended bursa illustrated. The drainage device is shown inserted into the bursa at the proper point and angle as instructed by the template.

A cannulated needle may be used with the template to facilitate drainage of the distended bursa. The cannulated needle includes a rigid needle and a cannula. The cannula is flexible so as to allow manipulation within the bursa without causing excess discomfort.

The rigid needle is inserted through the cannula and has a sharpened point for hypodermic insertion into the fluid filled bursa. Once inserted, the rigid needle is withdrawn, leaving the flexible cannula inserted in the bursa. The cannula has a leading end and a trailing end wherein the trailing end has an adapter for attachment onto a hypodermic syringe in order to drain the bursa of fluid.

The cannula leading end contains apertures spaced around its circumference. These apertures help reduce the chance of the cannula becoming blocked by contact with the inside wall of the bursa or clogged by solid material contained within the fluid.

It is therefore an object of this invention to describe a template used to instruct proper sites and technique for draining a human knee bursa that has become filled with fluid. A further object is to describe a cannulated needle to facilitate drainage of a fluid filled bursa which reduces discomfort to the patient and is resistant to blockage or clogging.

BRIEF DESCRIPTION OF THE DRAWINGS

FIG. 2 is a side elevational view of the cannulated needle for use with the template of this invention.

FIG. 3 is a side elevational view of the rigid needle of the cannulated needle of FIG. 2.

FIG. 4 is a side elevational view of the cannula of the cannulated needle of FIG. 2.

FIG. 5 is an enlarged view of section 5 of FIG. 4.

FIG. 6 is a view taken along the line 6—6 of FIG. 5.

DETAILED DESCRIPTION OF THE PREFERRED EMBODIMENT

Figure 1:
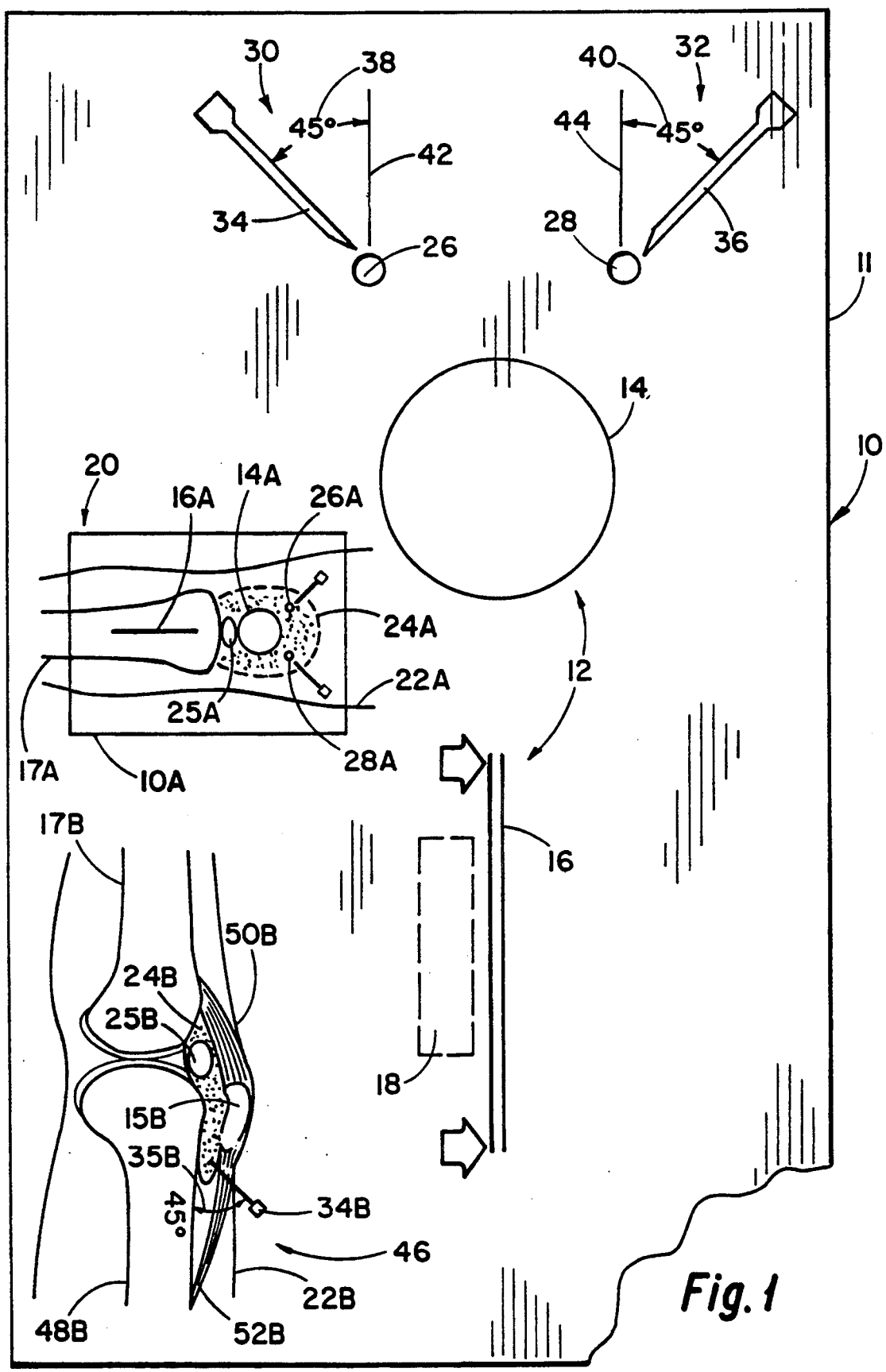
FIG. 1 is a top plan view of the template of this invention.

The drawings represent the present invention wherein FIG. 1 shows a top plan view of the preferred embodiment of the template of this invention, generally 10. Template 10 may be constructed from any suitable flexible sheet of material 11 so that it may be folded for packaging and transport and then later unfolded and draped over a patient's leg for use. Template 10 is universal as it may be used on either a right or left knee regardless of the size of the patient and has indicia thereon for locating it on a human leg over a patient's knee. Template 10 has indicia thereon for locating it on a human leg over a patient's knee, patella indicium 14 and tibia indicium 16. Patella indicium 14 is circular to illustrate the patella of the knee of a human leg. Tibia indicium 16 is defined by a pair of parallel lines used to orient template 10 over the leg. Tibia indicium 16 also includes tibia alignment instructions 18 so that the user of template 10 knows to align tibia indicium 16 on the crest of the tibia of the human leg.

Template 10 also includes insertion indicia 26 and 28. Insertion indicia 26 and 28 are holes cut in the template to identify the proper sites for hypodermic insertion of a device to drain a bursa of the knee which is filled with fluid, or distended.

Template 10 may also include a plan view diagram, generally 20, illustrating template 10 draped over a human leg. For the purpose of clarity in this description, reference numerals on plan view diagram 20 are the same as the reference numerals used in the general description of template 10 designating like elements. Like elements on plan view diagram 20, however, are distinguished by the letter "A".

Plan view diagram 20 depicts template 10A as it is properly placed over human leg 22 having a distended bursa 24A. A diagram such as plan view diagram 20 may be placed on template 10 for instructional purposes, or it may be placed on printed material which would accompany template 10.

Patella indicium 14A is overlaid upon the patella (not shown in plan view diagram 20) of the patient's knee. Likewise, tibia indicium 16A is overlaid upon the crest of the tibia 17A of leg 22A. When patella indicium 14A and tibia indicium 16A are properly overlaid upon the corresponding anatomical features of leg 22A (the patella and tibia 17A), insertion indicia 26A and 28A identify the proper sites for insertion of the device to drain distended bursa 24A.

As seen on plan view 20, 26A and 28A are the proper sites for insertion of a drainage device because of the presence of a fat pad 25A located below patella 14A. If a drainage device, such as a needle, were to be inserted at the point of fat pad 25A and fluid drained, the fat pad would be drawn to and block the end of the needle. This is the same principle upon which a ball valve operates, thereby preventing any further fluid drainage.

Once the proper sites for insertion, as identified by insertion indicia 26 and 28, are located, the draining device may be inserted at either point 26 or 28. In order to instruct proper angular insertion of the draining device, angular indicia 30 and 32 are placed on template 10. Angular indicia 30 and 32 include illustrations of draining devices 34 and 36, angular instructions 38 and 40, and reference lines 42 and 44. Angular indicia 30 and 32 instruct the physician that the proper angle for insertion of a drainage device, either 34 or 36, is 45° (or the proper angle instructed as 38 or 40) from its corresponding reference line 42 or 44. As illustrated in FIG. 1, the proper angle of insertion of needle 34 is 45° toward patella 14 from reference line 42.

Template 10 may also include lateral view diagram 46. For the purposes of clarity in this description, reference numerals on lateral view diagram 46 are the same as the reference numerals used in the general description of template 10, distinguished by the letter "B", to describe like elements. Lateral view diagram 46 is a lateral cut-away of leg 22B depicting the proper point and angle of insertion of draining device 34B. Lateral view diagram 46 illustrates tibia 17B, femur 48B, patella 15B, tendons generally 50B and 52B, and distended bursa 24B. Draining device 34B is properly inserted in lateral view diagram 46 such that it is inserted into leg 22B through tendon 52B at the proper angle instructed by template 10.

A second angular indicium 35B instructs the proper angle of insertion of the draining device 34B in relation to femur 48B. As can be seen on lateral view diagram 46, draining device 34B is inserted at a 45° angle from femur 48B.

Draining device 34B is shown entering distended bursa 24B in order for distended bursa 24B to be drained of fluid. It is understood that a diagram, such as lateral view diagram 46, may be placed on template 10 or may be included with printed material which would accompany template 10 for instructional purposes.

FIG. 2 depicts the cannulated needle 54 of this invention for insertion into, and draining of, a distended bursa. Cannulated needle 54 is particularly suited for use with template 10 of FIG. 1 to drain a distended knee bursa as described herein. It is understood, however, that cannulated needle 54 is useful for drainage of bursa other than knee bursa.

Cannulated needle 54 includes a rigid needle 56 and cannula 59. Rigid needle 56, as shown partially in phantom in FIG. 2, is inserted the length of cannula 59. Cannula 59 has a leading end 60 and a trailing end 62. The leading end 60 of cannula 59 contains a plurality of apertures therein.

In use, cannulated needle 54 is inserted at the proper site and angle of the patient's leg as identified by template 10 of FIG. 1. Point 57 of rigid needle 56 extends beyond cannula 59 and is sharpened to facilitate insertion. Once cannulated needle 54 is inserted into the leg at the proper site and angle, leading end 60 of cannula 59 is inserted into the fluid in the bursa. Rigid needle 56 is then withdrawn from cannula 59, leaving cannula 59 inserted in the bursa. A hypodermic syringe (not shown) is attached to trailing end 62 of cannula 59. Fluid is then drained from the bursa through cannula 59 into the barrel of the syringe by the vacuum created from withdrawing the syringe plunger.

FIG. 3 depicts rigid needle 56 removed from the cannula. Rigid needle 56 includes point 57 and hub 58. As stated, point 57 facilitates penetration of needle 56 into the distended bursa. Hub 58 is designed on one end to insert into the locking tip on the barrel of a hypodermic syringe and on its other end into the trailing end 62 (of FIG. 3) of cannula 59. Hub 58 is of a length so as to be held by the physician for insertion into the leg in the event insertion into a hypodermic syringe is not desired. Rigid needle 56 is tubular in order to allow drainage of fluid without withdrawing it from the cannula.

FIG. 4 shows cannula 59 with rigid needle 56 of FIG. 2 removed. Cannula 59 is made up of leading end 60, body 64, and trailing end 62. Trailing end 62 includes an adapter 66 into which either needle hub 58 of FIG. 3 or the locking tip of a hypodermic syringe is fit. A flexible member 68 connects cannula 64 with adapter 66.

The procedure of inserting a draining device and draining a knee bursa of fluid can cause a great amount of discomfort to the patient because of blind probing into the bursa walls with the sharp needle point. Body 64 of cannula 59 of the present invention is flexible so that as the bursa is being drained of fluid, body 64 can be manipulated within the bursa to access the greatest amount of fluid without being overly invasive.

FIG. 5 is an enlarged view of leading end 60, section 5 of FIG. 4. Leading end 60 is blunt so that as the bursa contracts from fluid being drained, leading end 60 will not stick into the bursa inner wall if contact is made.

Leading end 60 contains a plurality of apertures, or holes, 68, 70, 72, and 74. FIG. 6 is a cross-sectional view taken along line 6—6 of FIG. 5 showing that apertures 68, 72, 76, and 78 are drilled completely through wall 80 of leading end 60. Apertures 68, 72, 76, and 78 may be drilled around the circumference of circular leading end 60.

Referring back to FIG. 5, if the open end 80 of circular leading end 60 becomes blocked by contact with the inner wall of the bursa or clogged by solid material in the fluid, drainage of the bursa can be maintained through apertures 68, 70, 72, and 74. Likewise, if aperture 68 becomes blocked or clogged, fluid can still drain through apertures 70, 72, 74, and the open end 80. It should be understood that the number of apertures in circular leading end 60 could vary as required. In addition, the placement or shape of these apertures should not be limited by this description or the accompanying drawings. Any number of suitable shapes or placement or apertures could be employed to prevent complete clogging or blockage of leading end 60.

While the invention has been described with a certain degree of particularity, it is manifest that many changes may be made in the details of construction without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. A template for instructing proper insertion of a means for draining a distended bursa, comprising:
    a flexible sheet;
    indicia on said flexible sheet illustrating anatomical features of the human leg so that the flexible sheet may be overlaid upon the leg;
    means for identifying proper insertion of the draining means.

2. The template of claim 1 wherein said means for locating said flexible sheet also includes at least one diagram of the human leg with the template thereon.

3. The template of claim 1 wherein said means for identifying proper insertion of the means for draining a distended bursa includes:
    indicia on said flexible sheet illustrating proper sites of insertion of the means for draining a distended bursa such that when said indicia illustrating anatomical features of the human leg are overlaid upon the leg, said indicia illustrating proper sites of insertion of the means for draining a distended bursa will overlay the proper sites on the leg for insertion of the means for draining a distended bursa.

4. The template of claim 3 wherein said means for identifying proper instruction of the means for draining a distended bursa also includes indicia on said flexible sheet illustrating proper angles of insertion of the means for draining a distended bursa.

5. An apparatus for identifying a set of sites for proper hypodermic insertion into and for draining of a distended bursa in the knee of a human leg having anatomical features, comprising:
    a flexible sheet;
    means for draining the distended bursa;
    a first set of indicia on said flexible sheet illustrating anatomical features of the human leg so that said flexible sheet may be overlaid upon the corresponding anatomical features of the human leg;
    a second set of indicia on said flexible sheet illustrating proper sites of insertion of said draining means such that when said indicia illustrating anatomical features of the human leg are overlaid upon the leg, said second set of indicia overlay the proper sites on the leg for insertion of said draining means.

6. The apparatus of claim 5 including at least one diagram on said flexible sheet illustrating the human leg with the template properly overlaid thereon.

7. The apparatus of claim 5 wherein said second set of indicia also includes indicia illustrating proper angles of insertion of said draining means.

8. The apparatus of claim 7 including at least one diagram on said flexible sheet illustrating the human leg with the template properly overlaid thereon and said draining means inserted into the bursa at a proper site and angle.

9. The apparatus of claim 5 wherein said means for draining the distended bursa includes:
    a flexible tubular cannula having a leading end and a trailing end;
    said cannula having at least one aperture on its leading end;
    a rigid needle extending through said cannula for hypodermic insertion into the distended bursa.

10. An apparatus for identifying a set of sites for proper hypodermic insertion into and for draining a distended bursa in the knee of a human leg having a patella and tibia, comprising:
    a flexible template;
    a cannulated needle for hypodermic insertion into and draining of the distended bursa;
    a first set of indicia on said flexible template illustrating the patella and tibia so that said first set of indicia may be overlaid upon the patella and tibia of the human leg;
    a second set of indicia on said flexible template illustrating proper sites and angles of insertion of said cannulated needle into the distended bursa such that when said first set of indicia are overlaid upon the human leg, said second set of indicia overlay the proper sites on the leg for insertion of said cannulated needle.

11. The apparatus of claim 10 wherein said cannulated needle for hypodermic insertion into and draining of the distended bursa includes:
    a flexible tubular cannula having a leading end and a trailing end;
    said cannula having at least one aperture on its leading end;
    a rigid needle extending through said cannula.

12. The apparatus of claim 11 including at least one plan view diagram on said template illustrating the human leg with the template properly overlaid thereon and said cannulated needle inserted into the bursa at a proper site and angle.

13. The apparatus of claim 10 including at least one lateral view diagram on said template illustrating the human leg with the template properly overlaid thereon.

* * * * *